(12) United States Patent
Hirschbeck et al.

(10) Patent No.: US 8,504,588 B2
(45) Date of Patent: Aug. 6, 2013

(54) AUTOMATIC STUDY LINKING FOR HYBRID IMAGING

(75) Inventors: Frank Hirschbeck, Erlangen (DE);
Ehsanollah Mozaffarian, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 298 days.

(21) Appl. No.: 12/709,622

(22) Filed: Feb. 22, 2010

(65) Prior Publication Data
US 2011/0208764 A1    Aug. 25, 2011

(51) Int. Cl.
*G06F 17/30*    (2006.01)
(52) U.S. Cl.
USPC ............ 707/791; 707/802; 707/822; 707/828
(58) Field of Classification Search
USPC ................................................ 707/600–899
See application file for complete search history.

(56) References Cited

U.S. PATENT DOCUMENTS 7,853,621 B2 * 12/2010 Guo ............................... 707/803
2007/0118540 A1 * 5/2007 Guo ............................... 707/100

* cited by examiner

*Primary Examiner* — Isaac M Woo
(74) *Attorney, Agent, or Firm* — Harness, Dickey & Pierce, P.L.C.

(57) ABSTRACT

A method and an apparatus are disclosed for automatically linking at least two medical studies which are associated to different acquisition modalities (CT/PET) and which are subject of post-processing in the context of hybrid imaging. In a preparation phase of at least one embodiment, there is defined a classification scheme according to pre-definable rules, conditions and attributes. In an execution phase for a selected source study of a first modality there is looked for at least one target study of a second modality of the same type according to the rules. Then, the source study is automatically linked to the at least one target study.

14 Claims, 2 Drawing Sheets

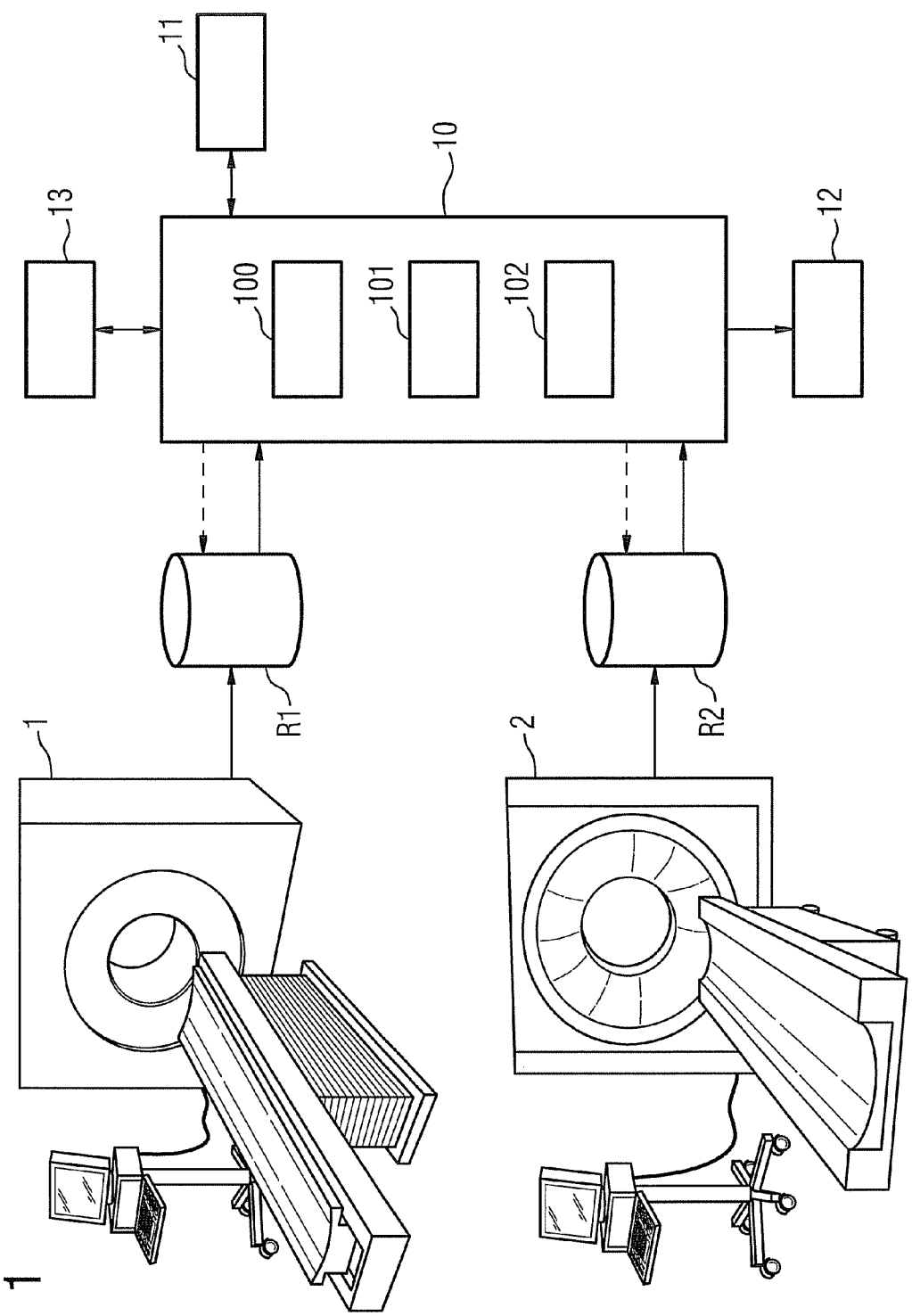

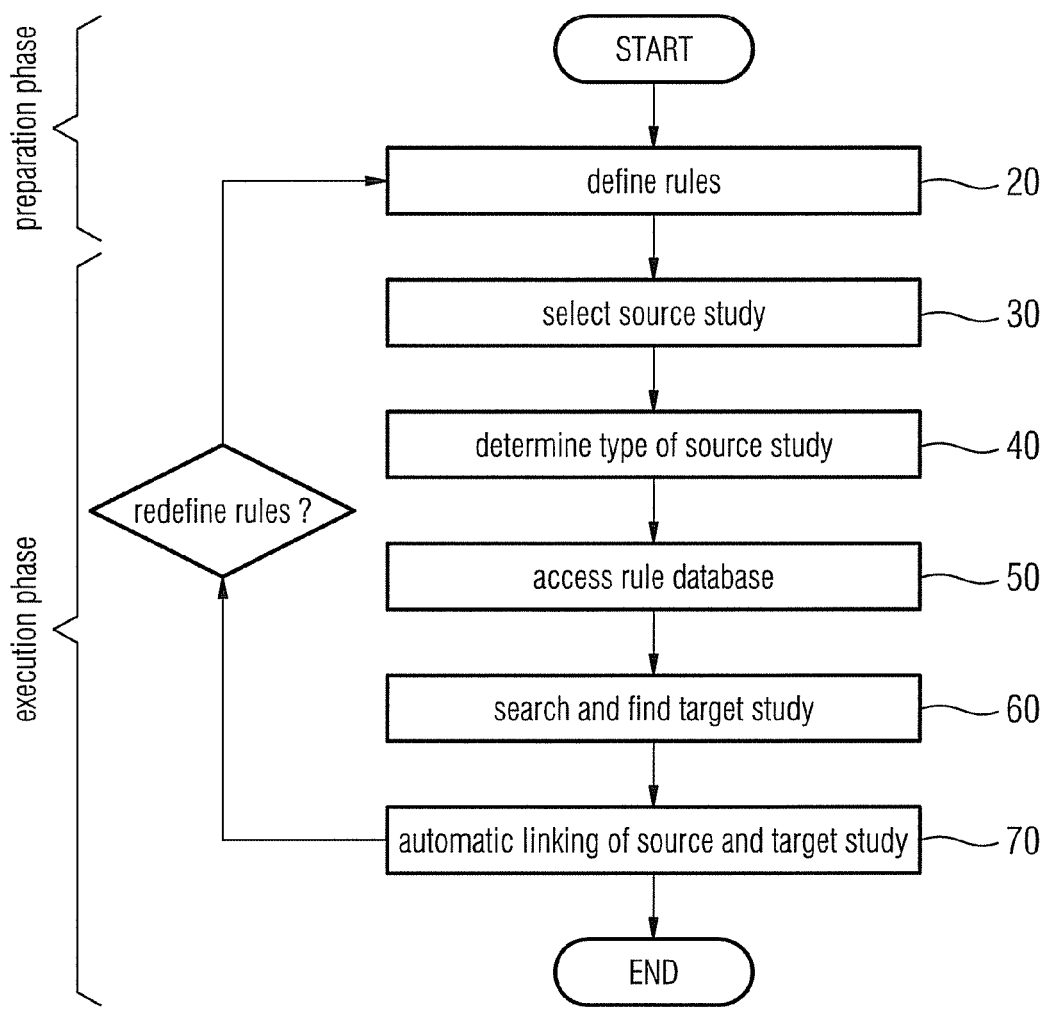

AUTOMATIC STUDY LINKING FOR HYBRID IMAGING

FIELD

At least one embodiment of the present invention generally relates to fields of medical imaging and data processing and particularly to a method and/or system for automatically, electronically linking studies of different types, i.e. stemming from different modalities, like CT (Computer Tomography), PET (Positron Emission Tomography), MRI (Magnetic Resonance Imaging) etc.

BACKGROUND

In state of the art systems it is known to use images of different types and from different modalities for different medical tasks, like post-processing or diagnostic tasks. If a physician needs to access images from different modalities up to now it was necessary to manually combine the data sets. However, in order to manually combine two studies, the physician needs to have specific knowledge with respect to data retrieval. For example he needs to know unique identifiers for accessing the data. It is therefore comprehensible that this known procedure is error prone and may—as a consequence—also lead to severe failures with respect to diagnosis, for example because the manual combination of studies relate to different patients.

Particularly in the field of hybrid imaging, which might be based on a PET modality and a CT modality there do not exist any proposals to automatically associate studies of different types in electronic form.

SUMMARY

Therefore a problem to be solved by at least one embodiment of the invention is to avoid wrong associations of medical studies.

Based on the drawbacks of the state of the art systems mentioned above it would be helpful to provide a computer-based automation tool for identifying medical studies to be processed or reviewed in common for the purpose of any one of different post processing tasks. Hence, linking information referring to the question according to which rules studies should be linked, should be detectable form the content of the study data itself and thus automatically and not only by user analysis. Hence, there is a need for a classification scheme and a rule database according to which studies are electronically classified and afterwards linked according to their classification or type. Moreover, there is a need for providing a data structure in which linking information could be stored, retrieved, updated and used for later processing.

The method according to at least one embodiment of the present invention allows for automatically associating at least two medical studies which belong to different medical acquisition modalities (for example to a CT modality and a PET modality) and which should be subject of further processing (which might be a post-processing, tasks in the field of diagnosis or reporting) in the context of hybrid imaging.

The method of at least one embodiment may include:
  selecting a source study of a first modality;
  determining a type of the selected source study, wherein the parameters for defining the type are pre-defined;
  accessing a set of rules for linking at least one target study of a second modality to the selected source of the first modality, wherein the target study and the source study belong to the same type;
  linking the source study to the found target study (or target studies, in case several target studies have been found) for the purpose of post-processing.

Hence, at least one repository is accessed in which the source study is stored. Thereinafter a rule database is accessed for detecting which rules apply to the source study in order to find at least one target study to be linked with the source study. Based on this linking information the at least one target study in the repository is accessed. The linked studies may then be processed in common. In addition it is possible to store the linking information within one of the studies, both of the studies or in a separate storage for linking information.

Generally, there is no limitation for a specific kind of modality, so that different modalities might be used, like PET, CT, SPECT, MR, US or other modalities.

It is also possible to define sub-types of modalities, like functional procedures, for example referring to functional PET, multi-functional PET/CT etc.

According to an aspect of at least one embodiment of the present invention there is defined a structure for classifying the acquired images for the acquired medical studies. In the classification scheme there is used a unique classifier which is bijectively associated to type of studies.

Within the classification scheme for defining a type of study at least two attributes are used:
  patient identity and
  acquisition date, wherein the latter may refer to time interval for data acquisition.

According to a further aspect the studies are stored or processed in a specific medical format, for example in a DICOM format, so that the above-mentioned attributes, classifiers, rules or conditions relate to DICOM attributes.

As already mentioned above the main intension of at least one embodiment of the present invention is to automatically associate studies of different types for the purpose of post-processing or reading.

According to a major aspect the linking is executed automatically, i.e. without user interaction. In an alternative embodiment it is also possible to automatically provide a suggestion for linking studies. However, a user confirmation is required for confirming this suggestion.

According to the specific application of at least one embodiment of the invention it is possible to provide a symmetric or asymmetric linking. In this respect the term "symmetric" refers to a bilateral association, so that there is a relation from the source to the target study and from the target study to the source study. For example there is provided a link from a PET-study to a CT-study and additionally there is provided a link from the CT-study to the PET-study. Whereas, the term "asymmetric" refers to a unilateral interrelation. In the example referred to above there is only provided a link from the PET-study to the CT-study and no further link.

The classification scheme and the rules for linking different study types are adaptable according to the present use case or implementation of the method according to at least one embodiment of the invention. With this feature it is possible to adapt or fit in the method according to medical requirements and specific context situation.

All these definition parameters, attributes and values for example for defining the rules, the conditions or other items are pre-definable in a preparation phase, which precedes an execution phase, in which the method is carried out, so that different studies of different types are linked. In case the preconditions for linking are updated it is possible to automatically trigger a new run for linking studies, because possibly other studies will be related according to the new linking preconditions.

According to another aspect of at least one embodiment of the present invention it is possible to store and to update linking data. With this feature it is possible to store information about the fact that the specific source study has been associated to a target study. Particularly, this is done in the respective study itself. For example it is possible to store private attributes in at least one of source study and target study or in both the studies. For later retrieval of this study this linking information is also accessible. The linking information might be accessible automatically or by user request.

According to a further aspect of at least one embodiment of the present invention the linking is done by providing and storing a private attribute in at least one of the source or the target study, wherein the private attribute refers to the respective other study which should be linked to the actual study. Particularly, this is done by way of a unique identifier. For example if a target study T has to be linked to a source study S, then it might be possible to store a private attribute with a unique identifier for the target study T in the DICOM header of the source study in the sense of "linking to target study T".

Alternatively, it is possible to store such linking information in the target study in form "linking with source study S". Also, a combination of the two possibilities mentioned above is possible, so that in each study there is stored linking information.

According to a further aspect of at least one embodiment of the present invention the method is integrated in a post-processing system (which may be a software tool) or is provided as an extension module of post-processing systems in order to provide a possibility for hybrid imaging. According to this, needless separate findings (including medical reports or diagnostic analysis) will be avoided.

At least one embodiment of the invention may be integrated as linking module in a PACS (Picture Archiving and Communication System) environment and/or into a post-processing workstation.

The solution according to at least one embodiment of the invention may have several advantages.

Apart from avoiding separate individual findings it is possible to enhance quality of medical finding and medical reporting as the evaluation can be based on a broader data basis (for example on images of different modalities). Moreover, it is no longer necessary to manually select different studies for the purpose of combined processing. The 'togetherness' is detected automatically.

Up to now, embodiments of the invention have been described with respect to the method. However, embodiments of the invention also might be implemented in hardware or in hardware modules combined with software modules. The hardware modules are then adapted to perform the functionality of the steps of the method, described above. Accordingly, it is also possible to have a combination of hardware and software modules. The modules are preferably integrated into an existing medical environment, for example into a PACS or RIS (Radiological Information System) or HIS (Hospital Information System).

According to an aspect of at least one embodiment of the invention there is provided a specific data structure for processing (including retrieving) linking information. Linking information is stored in an extended DICOM data structure with a reference tag for linked or referenced studies. Accordingly, the user will easily see all the referenced parallel studies which have been taken for the same patient and within the same acquisition time interval, in case he accesses a source study. The data structure causes functional change in computer execution as the studies may be processed in common automatically.

Another aspect of at least one embodiment of the invention is to be seen in a computer program being loadable in a memory of a computer, wherein the computer program is adapted to carry out the steps of the method as mentioned above.

BRIEF DESCRIPTION OF THE DRAWINGS

The figures illustrate principles of the invention according to specific embodiments. Thus, it is also possible to implement the invention in other embodiments, so that these figures are only to be construed as examples. Moreover, in the figures, like reference numerals designate corresponding modules or items throughout the different drawings.

FIG. 1 is a schematic block diagram according to one embodiment of a computer implemented system used within a medical system;

FIG. 2 is a flowchart diagram according to one embodiment of a method for automatically linking medical studies of different type.

DETAILED DESCRIPTION OF THE EXAMPLE EMBODIMENTS

In the following there is given a short explication and definition of terms, used in this disclosure.

The term "linking" is to be construed generically in the sense of electronically associating different datasets. According to an aspect of an embodiment of the invention the linking is executed fully automatic, so that it is possible to execute the linking without any user interaction. However, the feature "without any user interaction" is not mandatory, so that it is also possible to implement a confirmation module which is adapted to detect user interaction and input signals with respect to specific linking features. Generally, the linking refers to an automatic assignment or allocation of datasets, wherein the datasets refer to different studies, which have been acquired by different types of modalities. The linking information may be used for referencing medical datasets.

The term "study" refers to the meaning which is used within the DICOM standard. Thus, a "study" mainly is to be construed in the DICOM context but may also comprise or relate to different series of images. In the standard details with respect to data processing are regulated in case a specific patient undergoes a specific examination with an image modality, like PET, CT, MRI, US etc. It is possible to acquire for one patient several studies. The studies may refer to the same type of modality or two different types. The example for the latter possibility is that patient $P_1$ has been examined with a PET which leads to the study $S_1$ and moreover the same patient $P_1$ has been examined by the CT modality, which leads to the study $S_2$ and so forth. Generally, the term "study" refers to a completed examination of a patient, wherein the result of the examination is stored in datasets which are united as a study. A study may be subdivided into several serials, wherein one serial may comprise at least one image or one image data instance. In this respect it has to be noted that within the DICOM format a file of an image (for example an X-ray image of a knee) is intrinsically tight to a patient identification within the same file, so that the image data can never be separated from a patient identification data (normally stored within other metadata) by mistake.

If one patient has to undergo several examinations, the result of these examinations should be stored as different studies in a database. Each study is uniquely accessible by a unique identifier. Each type of study (usually comprising a plurality of studies) is uniquely accessible by a so called classifier. Thus, there exists just one classifier for just one type of study.

"Type of study" refers to a classification scheme that structures or classifies different instances of a study in different sets. According to an aspect of an embodiment of the invention the classification is flexibly adaptable, so that rules may be defined, redefined or modified for (amended) study classification. According to an embodiment of the invention a type of study is defined by two attributes:

1. Patient identity (two studies belong to the same type of study if and only if the patient is identical) and
2. Acquisition date (two studies belong the same type of study if and only if the acquisition date of these studies is within a pre-definable interval). This feature relates to the fact that the time of acquisition between two studies should correspond to each other within a pre-definable tolerance range. For example if one physician acquires image data (for example an X-ray image of a patient's chest) on Monday and another physician takes a second X-ray image of the same patient's chest one day after (on Tuesday), it probably will be useful to define these datasets as belonging to the same type of study, whereas if the acquisition time for example differs about several months, the corresponding image datasets probably will be classified in different types of study.

One skilled in the relevant art will easily recognize, however, that it is also possible to define more than the two above-mentioned attributes (patient identity and acquisition date). Further attributes may, for example, refer to acquiring physician, to hospital, to patient's disease or to other parameters.

The "set of rules" refers to the linking of a source study to at least one target study. For example a rule might be: "IF <source study classifier> EQUALS <target study classifier> THEN <linking source to target study>". Within these rules there may be defined conditions. Based on the classifiers, conditions may defined with may comprise further preconditions for a linking. Generally, it may be defined at least one condition. The condition may be patient-related, study-related, acquisition-related, modality-related, department-related or may relate to other medical items.

The linking is generally not restricted to 1:1-linking. Therefore, it is also possible to combine one source study to several target studies, in case the target studies all fulfill the conditions and rules, which have been pre-defined.

In the following description there will be described embodiments of a method and system for automatically linking at least two medical studies for the purpose of post-processing. The meaning of specific details should be construed as examples within the embodiments and are not exhaustive or limiting the invention to the precise forms disclosed within the examples. One skilled in the relevant art will recognize that the invention can also be practiced without one or more of the specific details or with other methods, implementations, modules, entities, datasets etc. In other instances, well-known structures, computer related functions or operations are not shown or described in detail, as they will be understood by those skilled in the art.

The method will be described with respect to DICOM image data. However, it is apparent that also other data formats and other image modalities or categories might also be applied and processed, respectively. Moreover, the method is described within the context of hybrid imaging. "Hybrid imaging" has to be construed generically as an approach to combine or to integrate different medical datasets into one combined set of data.

It is possible to incorporate biological datasets, nuclear medical datasets, radiological datasets, endoscopy-related sets with thermography-related datasets or microscopy-related datasets or combinations thereof. The datasets which have to be combined need not necessarily be image data and also might relate to electroencephalographic (EEG) data or to laboratory data.

It might also be possible to combine two forms of radiographic images, like projection radiography and fluoroscopy. Depending on the actual application other combinations might be useful. Therefore, a more complex embodiment refers to a linking of more than two studies, so that three or more different types of studies may be combined and linked for post-processing.

A main embodiment, however, refers to the combination of functional imaging (like PET, SPECT) and morphological imaging (like CT). In this respect it has to be noted that the invention is not limited to a specific embodiment, where (physically, at which modality) the image data have been acquired. Thus, it is possible that the different types of studies have been acquired at different modalities and, alternatively, it is possible that they have been acquired within one hybrid apparatus. Generally, the mapping between different types of studies (images) has the advantage that it is possible to overlay a medical lesion with the morphological information.

According to an embodiment of the invention it is possible to provide a combination of different types of medical studies for a specific medical question and thus combining the advantages of the different modalities (for example a high degree of patho-morphological information with high resolution for CT image and the advantage of monitoring metabolism within scarred tissue for PET image). With this, the post-image-acquisition workflow may be enhanced significantly, as all relevant data may be provided simultaneously.

The following discussion is intended to provide a brief, general description of a suitable computing environment (which might be of different kind like a client-server architecture or a internet/browser network) in which an embodiment of the invention may be implemented. An embodiment of the invention will be described in general context of computer-executable instructions, such as software modules, which might be executed in combination with hardware modules, being executed by different computers in the network environment. Generally, program modules or software modules include routines, programs, objects, instances, components, data structures etc. that perform particular tasks or implement particular abstract data types. Computer-executable instructions, associated data structures and program modules represent examples of the program code means for executing steps of the method described herein. The particular sequence of such executable instructions, method steps or associated data structures only represent examples of corresponding activities for implementing the functions described therein. For example the method comprises the steps selecting a source study, determining a type, assessing set of rules and linking. However, it is also possible to implement the method starting from a target study and searching for corresponding source studies which could be linked according to the set of rules with the target study. It is also possible to execute the method iteratively in order to have several linking runs for finding corresponding studies to a source study. Preferably, the several runs could be performed on distinct data repositories, for example in case the different studies stored in different repositories.

Those skilled in the art will appreciate that an embodiment of the invention may be practiced a network computing environment with many types of computer system configurations, including personal computers (PC), hand-held devices (for example like smartphones), multi-processor systems, microprocessor-based programmable consumer electronics, network PCs, minicomputers, mainframe computers, laptops and the like. An embodiment of the invention further may be practiced in distributed computing environments where computer-related tasks are performed by local or remote processing devices that are linked (either by hardwired links, wireless links or by a combination of hardwired or wireless links) through a communications network. In a distributed computing environment, program modules may be located in local or remote devices, memory systems, retrievals or data storages.

Generally, the method according to an embodiment of the invention may be executed on one single computer or on several computers that are linked over a network. The computers may be general purpose computing devices in the form a conventional computer, including a processing unit, a system memory, and a system bus that couples various system components including system memory to the processing unit. The system bus may be any one of several types of bus structures including a memory bus or a memory controller, a peripheral bus and a local bus using any of a variety of bus architectures, possibly such which will be used in clinical/medical system environments. The system memory includes read-only memory (ROM) and random access memories (RAM).

A basic input/output system (BIOS), containing the basic routines that have the functionality to transfer information between elements within the computer, such as during start-up, may be stored in one memory. Additionally, the computer may also include hard disc drives and other interfaces for user interaction. The drives and their associated computer-readable media provide non-volatile or volatile storage of computer executable instructions, data structures, program modules and related data items. A user interface may be a keyboard, a pointing device or other input devices (not shown in the figures), such as a microphone, a joystick, a mouse.

Additionally, interfaces to other systems might be used, such as an interface to a radiological information system (RIS) or to a hospital information system (HIS). These and other input devices are often connected to the processing unit through a serial port interface coupled to system bus. Other interfaces include a universal serial bus (USB).

Moreover, a monitor or another display device is also connected to the computers of the system via an interface, such as video adapter. In addition to the monitor, the computers typically include other peripheral output or input devices (not shown), such as speakers and printers or interfaces for data exchange.

Local and remote computer are coupled to each other by logical and physical connections, which may include a server, a router, a network interface, a peer device or other common network nodes. The connections might be local area network connections (LAN) and wide area network connections (WAN) which could be used within intranet or internet. Additionally networking environment typically includes a modem, a wireless link or any other device/method for establishing communications over the network.

Moreover, the network typically comprises device/method for data retrieval, particularly for accessing data storage devices like repositories and the like. Network data exchange may be coupled means of the use of proxies and other servers.

It has to be pointed out that the method changes and transforms physical subject matter as studies are stored differently, namely with a reference tag (indicating the linked or target studies) in a modified data structure of a source study.

FIG. 1 and the following discussion are intended to provide an example description of a suitable computing environment in which an embodiment of the invention may be implemented. On the left-hand side in FIG. 1 there are depicted the different modalities, a first modality 1 and second modality 2. The first modality 1 might be a computertomograph (CT) and the second modality 2 might be positron emission tomograph (PET).

One skilled in the art will recognize that it is possible to use other modalities or to extend the modalities so that more than two modalities may be used as input. Typically, the modalities 1, 2 are related to computing devices, which in FIG. 1 are depicted as a schematic representation of computers. The data which are acquired at the modalities 1, 2 are transferred to two repositories $R_1$, $R_2$. In FIG. 1 the repositories $R_1$, $R_2$ are separate repositories. However, it is also possible to use a common repository R for both the first modality 1 and the second modality 2 and possibly for any further modalities.

According to an embodiment of the invention the repositories $R_1$, $R_2$ are in data exchange with a linking module 10.

In the embodiment, depicted in FIG. 1, the linking module 10 is in data exchange with a processing unit 13 and with an input interface 11 and with an output interface 12, as well as with the different repositories $R_1$, $R_2$. However, it is apparent for one skilled in the art that on the one hand the linking module 10 may also have other physical or logical connections to other computer instances and on the other hand that a specific connection may not necessarily be provided. For example the processing unit 13 is not mandatory for execution of an embodiment of the invention.

In the embodiment of FIG. 1 the linking module 10 comprises other modules, like a selection module 100, a determination module 101 and an access module 102. These modules may be implemented in hardware or in software or in a combination thereof. Moreover, they may be integrated into one electronic device or implemented in separate devices. The selection module 100 is adapted for selecting a source study of the first modality 1 out of the repository $R_1$. The determination module 101 is adapted for determining a type of the selected source study. The access module 102 is adapted for accessing a set of rules stored in a repository (not depicted in FIG. 1).

The rule repository may also be part of the linking module 10 or alternatively may be coupled to the same by network connection. Moreover, the rule repository may be part of the repositories $R_1$, $R_2$. In the rule repository there are stored rules for linking studies of different modalities according to their type. The rules may be adapted to the specific application in order to find at least a target study of the second modality 2 for the selected source study (of the first modality 1), wherein the selected source study and the (at least one) target study are of corresponding type. Particularly, the types should be identical. The definition of types may be inputted by means of the input interface 11. Preferably, this is done in a preparation phase before a runtime phase.

The rules may comprise conditions and/or or parameters for linking studies of different type. Further, they relate to the categorization or classification of studies into different types of studies. The attributes used for categorization of studies into different types of studies are: patient identity and acquisition date. However, it is apparent that this is a very simple form for defining the type of study. Accordingly, also a more complex (finer granulated) definition may be used, which comprises the definition of further rules, conditions, subconditions, attributes or parameters.

The rules, the conditions, the attributes and parameters for defining a type of studies are defined in a preparation phase. This is done by a user by way of input interface 11. Therefore, a specific or several specific windows may be provided on the input interface 11 on which the user may chose several items or input values by way of the inputting devices as mentioned above. Preferably, there is provided a suggestion for pre-defined values for the rules, the conditions and/or the attributes. Then, the user only has to confirm these suggestions. Alternatively, he may change or amend the pre-defined suggestions with his own manually inputted parameters. After all necessary parameters have been inputted the linking module 10 may start working. Additionally, the linking module 10 may access a processing unit 13 for further data processing. Generally, the linking module 10 is adapted for automatically linking at least two medical studies which are associated to different medical acquisition modalities 1, 2 and which should be made subject for post-processing.

In this respect it has to be mentioned that the term "post-processing" has to be construed generically and also includes other actions like reading data, evaluating data (for example statistically), executing diagnostic tasks, executing tasks with respect to reporting etc. Apart from the above-mentioned tasks post-processing also refers to background activities in the field of data processing, for example for the purpose of quality improvement. In this case the post-processing includes routines like image scaling, multivariate interpolation, sub-sampling, zooming, conversion routines, interlacing, sharpening/softening routines, requantization routines etc.

The output or result of linking is that studies of different type are matched or assigned to each other according to the pre-defined rules. According to a normal use case, a selected source study is linked to one target study. However, it is also possible to have a manifold result in that a single source study is linked to several target studies. The result is outputted by way of the output interface 12.

The result of the linking may be of different kind. According to a first embodiment it is possible that in case a CT-study is transferred from the modality to a post-processing software module, the post-processing software module automatically detects that the CT-study has been linked to a target study, which might be a specific PET-study. In case the PET-study has to be displayed on a monitor according to an activity in later stage of the post-processing workflow the linked CT-study automatically will be provided, too. Accordingly, both studies will be evaluated in combination.

It is also possible to make the linking persistent (for example for future evaluations). Therefore, the linking data for linking the studies are stored as DICOM-tag. Accordingly, the linking information will be maintained during long term archiving procedures. For example if the PET-study will be accessed in the medical archive as a preliminary study for a follow-up examination, then the linked CT-study will also be taken into account automatically.

The rule repository stores a set of rules for linking different studies. Each rule consists of two classifiers: one classifier for a source study and a second classifier for a target study. According to one embodiment of the invention a classifier may be implemented as a set of DICOM attributes, wherein the attributes define the type of a study. The significant attributes (also called DICOM tags) are preconfigured according to the classification scheme (for example: "MODALITY" and "STUDY_DESCRIPTION").

For example a rule could be:
{MODALITY="PET"; STUDY_DESCRIPTION="PET Head"} (referring to the source classifier)
{MODALITY="CT"; STUDY_DESCRIPTION="CT Head"} (referring to the target classifier).

With respect to FIG. 2 a possible sequence of steps is described hereinafter. After starting, in step 20 relevant parameters and values may be defined via input interface 11. This step refers to the definition of rules, conditions, attributes and other parameters for the purpose of defining a type of study. Step 20 is executed in a preparation phase which precedes the runtime or execution phase. In the preparation phase all relevant values and parameters have to be detected for a categorization of studies. Usually the categorization is based on at least two attributes: 1. patient identity and 2. acquisition date. Accordingly, all studies which refer to the same patient and which have the same or a corresponding acquisition time belong to a same type of study.

The execution phase follows the preparation phase but is generally independent of the same and might be executed at any time after completing the preparation phase. In step 30 a source study of a first modality 1 is selected. Usually, this is done by the user manually via the input interface 11. However, it is also possible to detect the source study automatically by evaluating data sets, which have been read in from other resources.

In step 40 a type of source study is determined. This is done according to the predefined rules, conditions and attributes. Therefore, in step 50, the rule database is accessed for linking at least one target study to the selected source study.

Step 60 refers to searching and finding at least one target study for the selected source study according to the rules in the rule repository.

Finally, in step 70, there is an automatic linking of the source study to the at least one target study. Hereinafter the method ends.

In FIG. 2 a recursive application of several steps is depicted with the arrow starting from step 70 and detecting whether or not rules or other parameters have to be redefined. If yes, the method goes back to step 20 and starts again otherwise it ends. With this feature it is also possible to modify rules, conditions, attributes or other parameters relevant for linking, also during linking procedure is running or active.

Generally, there are two possibilities for displaying the referenced target studies: First, it is possible to additionally display all the referenced target studies automatically with the source study. Second, it is possible to only display icons, pictograms, widgets or miniature representations of the target study, which could be loaded upon user request.

In addition and as already mentioned above, it is also possible to store linking data for further procedures. This is depicted in FIG. 1 with the dashed lines starting from the linking module 10 and pointing to the repositories $R_1$, $R_2$. The dashed line should indicate that this step is not mandatory, although it might be helpful to store linking information in the respective studies in the repositories $R_1$, $R_2$ or in other computer instances or memories respectively.

According to an automated embodiment according to the invention the system is informed by a <new study message>, in case a new study or new series have been acquired at a modality 1, 2. In case the system is informed about image data there is automatically a classification of the newly arrived study according to the pre-defined classification scheme. Further, rules are selected which could be applied to the classified study wherein source classifier and target classifier may be taken into account equally.

With respect to the attribute, relating to the acquisition date it could be implemented that not only the exact acquisition date but a time interval has to be taken into account. A time interval might be a day unit. Accordingly, if a first study for the patient has been executed in the morning and if a second study for the same patient has been executed in the evening of the same day, then these two studies may be structured or classified into the same study. The length of the time interval may be configured.

In contrast to the embodiment described above, it is also possible to provide a separate rule repository, which is separate from the linking module 10 and also separate from the repositories $R_1$, $R_2$ (this embodiment is not depicted in the figures). This has the advantage that rule repository(ies) with rules, conditions and attributes may be amended and modified without touching the linking module 10.

Moreover, it is also possible to provide a central storage or repository for storing the studies with linking information relating to the studies.

The example embodiments are to be considered in all respects only as illustrative and not restrictive. The scope of the invention is, therefore, indicated by the appended claims rather than by this description. All changes which come within the meaning and range of equivalency of the claims are to be embraced within their scope.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

REFERENCE NUMERALS 1 first modality
2 second modality
$R_1$ repository for first modality
$R_2$ repository for second modality
10 linking module
100 selection module
101 definition module
102 access module
11 input interface
12 output interface
13 processing unit
20 defining rules, conditions, attributes
30 selecting source study of first modality
40 determining type of source study
50 accessing rule database for linking
60 searching and finding target study
70 automatic linking of source to target study

What is claimed is:

1. A method for automatically linking at least different two medical studies, associated to different medical acquisition modalities and are subject to post processing in the context of hybrid imaging, comprising:
  selecting, by a linking unit, a source study of a first modality;
  determining, by the linking unit, a type of the selected source study, the type referring to a patient and an examination date;

accessing, by the linking unit, a set of rules for linking the at least two different medical studies of different medical acquisition modalities according to respective types, to find for the selected source study at least a target study of a second modality of the same type of the selected source study, the source study and the target study being different studies; and linking, by the linking unit, the source study to the found target study for the purpose of post processing.

2. The method according to claim 1, wherein the modalities are selected of the group consisting of:

positron emission tomography (PET), computed tomography (CT), single-photon emission computed tomography (SPECT), magnetic resonance (MR), unconditional stimulus (US) or other modalities.

3. The method according to claim 1, wherein the determining of the study type is based on a classification, and wherein a classifier being unique for the type of study.

4. The method according to claim 1, wherein the selecting of the source study is executed for the purpose of post processing or other actions.

5. The method according to claim 1, wherein the linking is executed automatically or upon user confirmation.

6. The method according to claim 1, wherein the linking is symmetric or asymmetric.

7. The method according to claim 1, wherein at least one of the rules and conditions are definable in a preparation phase.

8. The method according to claim 1, wherein the linking comprises:

storing a private attribute in at least one of the source and target study with a unique identifier of the respective other study.

9. The method according to claim 1, wherein the studies are stored or processed in a DICOM format and the classifiers, rules or conditions relate to DICOM attributes.

10. The method according to claim 1, wherein the method is integrated in a post processing system or is provided as an extension of the post processing system.

11. The method according to claim 1, further comprising:

storing the linking between the source study and the at least one target study.

12. The method of claim 1, wherein the selecting is performed by a selection module, the determining is performed by a determination module, the accessing is performed by an accessing module and the linking is performed by a linking module.

13. An apparatus for automatically linking at least two different medical studies, associated to different medical acquisition modalities and are subject to post processing in the context of hybrid imaging, comprising:

a processing device configured to, select a source study of a first modality;

determine a type of the selected source study, the type referring to a patient and an examination date;

access a set of rules stored in a rules repository to link the at least two different medical studies of different medical acquisition modalities according to respective types, to find for selected source study at least a target study of a second modality of the same type of the selected source study, the source study and the target study being different studies; and link the source study to the found target study for the purpose of post processing.

14. A computer readable medium including program instructions which, when executed by a processor of a computer system, cause the processor to perform a method for automatically linking at least two different medical studies, associated to different medical acquisition modalities and are subject to post processing in the context of hybrid imaging, the method comprising:

selecting a source study of a first modality;

determining a type of the selected source study, the type referring to a patient and an examination date;

accessing a set of rules for linking the at least two different medical studies of different medical acquisition modalities according to respective types, to find for the selected source study at least a target study of a second modality of the same type of the selected source study, the source study and the target study being different studies; and linking the source study to the found target study for the purpose of post processing.

* * * * *